US012714370B2

(12) United States Patent
Wang et al.

(10) Patent No.: US 12,714,370 B2
(45) Date of Patent: Aug. 25, 2026

(54) FORCE-CONTROLLED ELECTROENCEPHALOGRAM MONITORING DEVICE

(71) Applicant: MICROSOFT TECHNOLOGY LICENSING, LLC, Redmond, WA (US)

(72) Inventors: Yu-Te Wang, Redmond, WA (US); Ivan Jelev Tashev, Kirkland, WA (US); Teresa Elizabeth Lascala, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1099 days.

(21) Appl. No.: 17/555,311

(22) Filed: Dec. 17, 2021

(65) Prior Publication Data

US 2023/0190196 A1 Jun. 22, 2023

(51) Int. Cl.
*A61B 5/291* (2021.01)
*A61B 5/00* (2006.01)
(Continued)

(52) U.S. Cl.
CPC .......... *A61B 5/6843* (2013.01); *A61B 5/0006* (2013.01); *A61B 5/265* (2021.01);
(Continued)

(58) Field of Classification Search
CPC ..... A61B 5/6803; A61B 5/0006; A61B 5/291; A61B 5/369; A61B 5/6843
See application file for complete search history.

(56) References Cited

U.S. PATENT DOCUMENTS

| | | | | |
|---|---|---|---|---|
| 8,103,328 | B2 * | 1/2012 | Turner | A61B 5/291 600/587 |
| 9,622,703 | B2 * | 4/2017 | Badower | A61B 5/316 |

(Continued)

FOREIGN PATENT DOCUMENTS

| | | | |
|---|---|---|---|
| CN | 111281380 | A | 6/2020 |
| WO | 2012153263 | A1 | 11/2012 |
| WO | 2015196554 | A1 | 12/2015 |

OTHER PUBLICATIONS

U.S. Appl. No. 17/555,278, filed Dec. 17, 2021.
(Continued)

*Primary Examiner* — Joanne M Rodden
*Assistant Examiner* — Alyssa M Pape
(74) *Attorney, Agent, or Firm* — Benjamin Keim; Newport IP, LLC

(57) ABSTRACT

A force-controlled electroencephalogram (EEG) monitoring device maintains a constant pressure between electrodes and the scalp of a user thereby increasing user comfort. Arms on the EEG monitoring device position the electrodes in contact with specific regions on the head of the user. The dimension, shape, and curvature of the arms affect the amount of force with which an electrode is held in contact with the user's scalp. The amount of pressure may be different for different regions of the user's head to achieve a balance between comfort and conductivity. The amount of pressure may be further modulated by the use of spring-loaded electrode holders that allow an electrode to move relative to the holder. To further improve user comfort, the tips of the electrodes may be hemispherical rather than pointed. The EEG monitoring device can be used as input for a brain-computer interface (BCI).

16 Claims, 9 Drawing Sheets

(51) Int. Cl.
*A61B 5/265* (2021.01)
*A61B 5/369* (2021.01)

(52) U.S. Cl.
CPC .............. *A61B 5/291* (2021.01); *A61B 5/369* (2021.01); *A61B 5/6803* (2013.01)

(56) References Cited

U.S. PATENT DOCUMENTS

| | | | | |
|---|---|---|---|---|
| 9,814,426 | B2 | 11/2017 | Connor | |
| 11,093,033 | B1 | 8/2021 | Wang et al. | |
| 2007/0255127 | A1 | 11/2007 | Mintz | |
| 2008/0154112 | A1 | 6/2008 | Murphy | |
| 2011/0074396 | A1 | 3/2011 | Liao | |
| 2012/0179062 | A1 | 7/2012 | Wilson | |
| 2013/0127708 | A1 | 5/2013 | Jung et al. | |
| 2016/0063874 | A1 | 3/2016 | Czerwinski et al. | |
| 2016/0081577 | A1* | 3/2016 | Sridhar | A61B 5/6803 600/383 |
| 2016/0120432 | A1 | 5/2016 | Sridhar | |
| 2016/0143554 | A1* | 5/2016 | Lim | A61B 5/6803 600/386 |
| 2018/0263523 | A1* | 9/2018 | Puttilli | A61B 5/0077 |
| 2018/0271416 | A1* | 9/2018 | Begtrup | A61B 5/14517 |
| 2019/0192030 | A1 | 6/2019 | Watson | |
| 2019/0192078 | A1 | 6/2019 | Sargent | |
| 2019/0231235 | A1 | 8/2019 | Jeong | |
| 2020/0107741 | A1* | 4/2020 | Fruitwala | A61B 5/291 |
| 2021/0240264 | A1 | 8/2021 | Wilson et al. | |
| 2023/0190175 | A1 | 6/2023 | Wang et al. | |

OTHER PUBLICATIONS

Non-Final Office Action mailed on Jan. 13, 2025, in U.S. Appl. No. 17/555,278, 17 pages.
Final Office Action mailed on Feb. 13, 2026, in U.S. Appl. No. 17/555,278, 28 pages.
Final Office Action mailed on Jun. 25, 2025, in U.S. Appl. No. 17/555,278, 24 pages.
Non-Final Office Action mailed on Aug. 8, 2025, in U.S. Appl. No. 17/555,278, 24 pages.

* cited by examiner

FORCE-CONTROLLED ELECTROENCEPHALOGRAM MONITORING DEVICE

BACKGROUND

Electroencephalography (EEG) is a method to record an electrogram of the electrical activity on the scalp that has been shown to represent the macroscopic activity of the surface layer of the brain underneath. It is typically non-invasive, with the electrodes placed along the scalp. EEG measures voltage fluctuations resulting from ionic current within the neurons of the brain. Many systems typically use electrodes, each of which is attached to an individual wire. Some systems use caps or nets into which electrodes are embedded; this is particularly common when high-density arrays of electrodes are needed.

In conventional scalp EEG, the recording is obtained by placing either wet or dry electrodes on the scalp. The conductivity between the electrodes and the scalp plays an important role in the quality of the signals generated by EEG. Higher conductivity lowers impedance and improves the signal-to-noise ratio (SNR) resulting in collection of more accurate data. Wet electrodes improve connectivity between the electrode and the scalp by using a conductive gel or paste. However, the conductive gel may require a technician to apply and can be difficult to remove from the hair and scalp. Conventional wet electrodes can be impractical outside of medical and research settings.

Some EEG systems use dry electrodes without conductive gel that depend upon mechanical contact. Dry electrodes are better suited for wearable devices and informal settings because they do not use messy conductive gel. However, dry electrodes typically have lower conductivity and lower SNR than wet electrodes. One approach to improve conductivity of dry electrodes is to use high levels of pressure to press electrodes towards the scalp. The high pressure helps force the electrode tips through the hair layer and make strong contact with the scalp. Yet, the high pressure and pointed tips of many dry electrodes can be uncomfortable for the user. This makes wearing conventual dry electrodes for long periods of time unpleasant and limits the applications of dry electrodes.

It would be desirable to have an electrode configuration for use in EEG as well as a wearable EEG monitoring device that provides good conductivity between the electrodes and the scalp without compromising comfort and ease of use. Such an electrode and EEG system would have many potential uses including in brain-computer interfaces (BCI). This disclosure is made with respect to these and other considerations.

SUMMARY

This disclosure provides a force-controlled EEG monitoring device that is comfortable for the user. The EEG monitoring device can be an EEG headset that has multiple dry electrodes each at the end of separate arms configured to hold the electrodes in contact with the scalp at a constant pressure. The size, shape, and curvature of the arms control the amount of force between the electrodes and the scalp when the EEG headset is worn. Different arms may be designed to apply different levels of force depending on where the electrode contacts the scalp of the user. This provides a balance between comfort and conductivity.

The electrodes may be contained in spring-loaded electrode holders. The spring-loaded electrode holders can be located at the ends of the arms of the EEG headset. Springs in the spring-loaded electrode holders allow an electrode to move relative to the holder. This helps to maintain the electrode in contact with the scalp at a constant pressure. Rather than an electrode pressing against the scalp with too much force, some of the excess force can be absorbed by the spring-loaded electrode holder.

In one configuration, the EEG headset includes a housing unit that sits on top of the head of the user when worn. The housing unit may contain electronics such as amplifiers, a digital-to-analog converter, and a wireless transmitter. The EEG headset includes a plurality of arms that may be attached to the housing unit. The arms extend outward from one or more sides of the housing unit and curve so that the ends of the arms hold electrodes in contact with the head of the user. The amount of force created by the curvature and shape of the arms may depend on the location on the head of the user contacted by the electrode. For example, an arm that holds an electrode in contact with the frontal region of the user's head may do so with an amount of pressure that is about 350-450 g/cm$^2$. An arm that holds an electrode in contact with the occipital region of the user's head may do so with an amount of pressure that is about 550-650 g/cm$^2$.

The electrodes themselves may be hemisphere shaped rather than pointed to ease uncomfortable sensations on the scalp. The hemisphere may be approximately 1.5-2.5 mm in diameter. The electrodes are made of a conductive material such as silver/silver chloride.

In one implementation, the EEG headset is a component of a system configured to implement a BCI. The wireless transmitter in the EEG headset may communicate electrical potential detected by the electrodes to a computing device. The computing device can then process the electrical potential as user input in a BCI system.

Features and technical benefits other than those explicitly described above will be apparent from a reading of the following Detailed Description and a review of the associated drawings. This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

The Detailed Description is described with reference to the accompanying figures. In the figures, the left-most digit(s) of a reference number identifies the figure in which the reference number first appears. The same reference numbers in different figures indicate similar or identical items. References made to individual items of a plurality of items can use a reference number with a letter of a sequence of letters to refer to each individual item. Generic references to the items may use the specific reference number without the sequence of letters.

DETAILED DESCRIPTION

Figure 1:
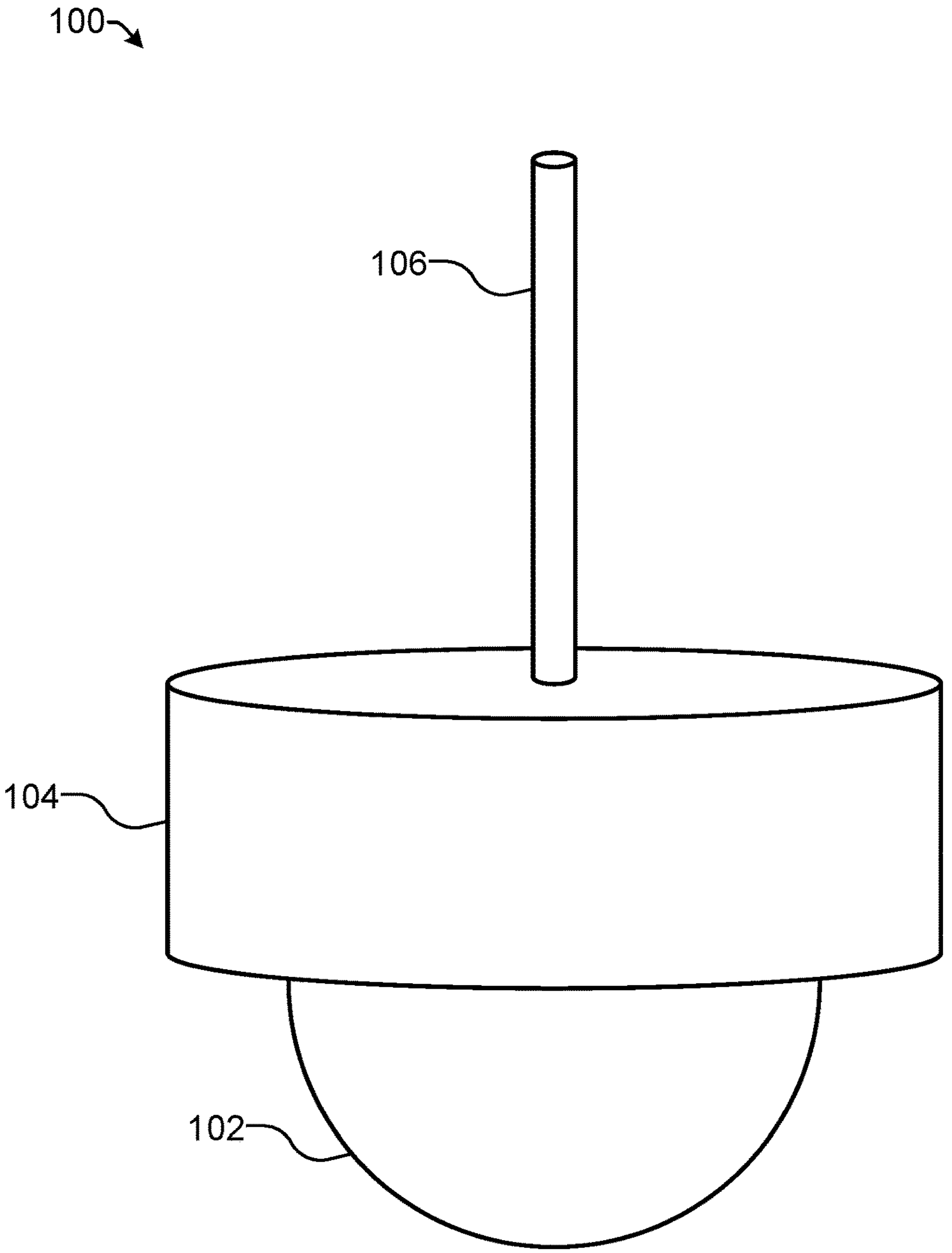
FIG. 1 is a diagram of a dry electrode with a hemispherical shaped tip.

FIG. 1 shows one illustrative configuration of a dry electrode 100 that has a hemispherical shaped tip 102. The hemispherical shaped tip 102 is more comfortable than a pointed tip because a smoothly curved surface contacts the scalp and can alleviate the discomfort sensation of skin abrasion. In one configuration, the hemispherical shape tip 102 extends from a disk 104 that provides a larger and more stable structure than the hemispherical shaped tip 102. Although illustrated as a disk 104, other shapes may be used to provide a point of connection to the hemispherical shaped tip 102. In some implementations, the disk 104 may be omitted. A rod or wire 106 may extend from the disk 104 and provide a conductive connection to an external circuit. In some implementations, the rod/wire 106 may be omitted and a different structure may be used to provide a conductive connection to the dry electrode 100. The external circuit may carry electrical potential from the electrode 100 to other components such as amplifier and/or data acquisition device. The electrode 100 may be used in an EEG headset and it may also be used for detecting electrical potential on other areas of the body besides the scalp.

The hemispherical-shaped tip 102, the disk 104, and the rod 106 are formed from a conductive material. Many types of conductive materials are known to those of ordinary skill in the art for use with EEG electrodes. Examples of suitable conductive materials include, but are not limited to, conductive metals or metal alloys such as gold, titanium, platinum, silver, copper, tin, nickel, and brass. Other suitable conductive materials include metal compounds such as, but not limited to, iridium-oxide and silver/silver chloride. Further examples of suitable conductive materials include carbon-containing materials such as, but not limited to, graphene and carbon nanotube polydimethylsiloxane. Techniques for forming electrodes from these types of materials are known to those of ordinary skill in the art. For example, a silver/silver chloride electrode may be formed by coating metallic silver with a thin layer of silver chloride. The thin layer of silver chloride may be created either by physically dipping the electrode in molten silver chloride, chemically by electroplating the electrode in concentrated hydrochloric acid (HCl), or electrochemically by oxidizing the silver at an anode in a chloride solution.

The hemispherical shaped tip 102, the disk 104, and the rod/wire 106 may all be formed from the same or from different conductive materials. For example, the hemispherical shaped tip 102, the disk 104, and the rod/wire 106 may all be made of silver/silver chloride. For example, the hemispherical shaped tip 102 and the disk 104 may be silver/silver chloride while the rod/wire 106 is formed from another conductive material such as silver. In a configuration, the hemispherical-shaped tip 102 and the disk 104 are formed from a single piece of material. In a configuration, the hemispherical shaped tip 102, the disk 104, and the rod/wire 106 are formed from a single piece of material.

With current manufacturing techniques, it can be difficult to create hemispheres with diameters smaller than about 2.0 mm. A hemisphere with a diameter greater than 5 mm may have difficulty penetrating the hair on the scalp of a user and contacting the scalp. Thus, to have a size that can be reliably manufactured and readily move between the hair to contact the scalp of a user, the hemispherical shaped tip 102 may have a diameter that is between about 1.0-5.0 mm or between about 1.5-2.5 mm. In one implementation, the diameter of the hemispherical shaped tip 102 may be about 2.0 mm. The disk 104 may also have a diameter that is less than about 5 mm so that it is also able to easily penetrate the hair of the user. For example, the disk 104 may have a diameter that ranges from the same as the diameter of the hemispherical-shaped tip 102 to about 5 mm (e.g., 2-5 mm). As used herein, "about," "around," "approximately," and similar referents indicate ±10% of the stated value.

Figure 2:
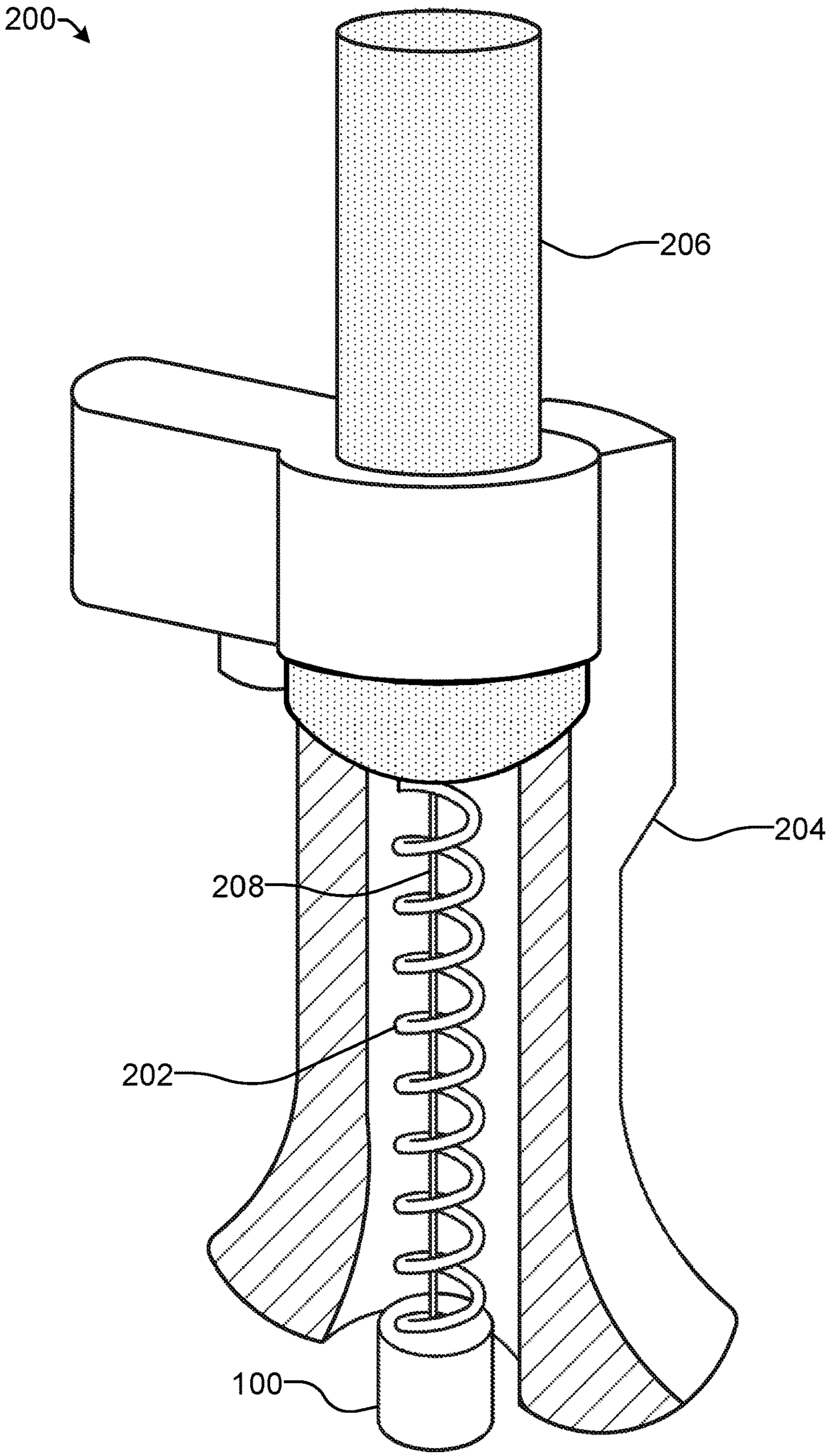
FIG. 2 is a partial cutaway diagram of a spring-loaded electrode holder.

FIG. 2 shows a partial cutaway view of a spring-loaded electrode holder 200. The spring-loaded electrode holder 200 may hold the electrode 100 shown in FIG. 1. Alternatively, the spring-loaded electrode holder 200 may be used with electrodes that have a shape other than hemispherical. The electrode 100 is attached to a spring 202. The spring 202 may be a compression spring that becomes shorter when force is applied to the tip of the electrode 100. In one implementation, the spring 202 is a coil spring. However, any type of spring 202 that allows the electrode 100 to move relative to the spring-loaded electrode holder 200 may be used. Examples of suitable spring types include flat springs, disk springs, and serpentine springs. The spring 202 may be formed of any type of material commonly used to create springs such as steel. The spring 202 may be formed from a conductive material or a nonconductive material.

Compression of the spring 202 absorbs force at the electrode 100 and prevents the electrode 100 from pressing into the skin of the user with too much force. The spring 202 is configured to maintain the electrode 100 in contact with the skin of the user with a constant amount of force thereby increasing user comfort. The amount of force may depend on where the electrode 100 contacts the head of the user. For example, if the electrode 100 is configured to contact the frontal region of the user's head, the spring 202 may be configured to maintain the electrode 100 in contact with the scalp with about 350-450 g/$cm^2$ or about 400 g/$cm^2$ of pressure. For example, if the electrode 100 is configured to contact the occipital region of the user's head, the spring 202 may be configured to maintain the electrode 100 in contact with the scalp with about 550-650 g/$cm^2$ or about 600 g/$cm^2$ of pressure.

The spring-loaded electrode holder 200 may include a housing 204 that partially or fully encases the spring 202. The housing 204 may be formed from a non-conductive material such as plastic. The housing 204 may protect the spring 202 and provide a rigid structure for the spring-loaded electrode holder 200. A base of the housing 204 may be flared to increase the area contact with the head of the user. The flared base may increase user comfort.

The spring 202 is also connected to an interface 206. The interface 206 provides a conductive connection to the spring-loaded electrode holder 200. The interface 206 is the point of connection to an external circuit that may include other components such as an amplifier and/or data acquisition device. The interface 206 is formed from a conductive material such as a conductive metal, for example, but not limited to silver or copper. There is a conductive connection between the electrode 100 and interface 206 so that electrical potential detected at the electrode 100 is carried to the interface 206. In an implementation, the conductive connection is a wire 208 between the electrode 100 and the interface 206. The wire 208 may be formed from any conductive material suitable for creating wires such as, but not limited to, silver or copper. The wire 208 may be the same as the rod/wire 106 shown in FIG. 1. In an implementation, the spring 202 may be formed from a conductive material and the spring 202 itself is the conductive connection between the electrode 100 and interface 206. In such an implementation, the wire 208 may be omitted.

Although suitable as a component of an EEG headset, the spring-loaded electrode holder 200 may also be used in other applications. For example, the spring-loaded electrode holder 200 may be used to hold electrodes in contact with portions of a user's body other than scalp such as for electrocardiography to detect electrical activity of the heart and produce an electrocardiogram (ECG) or to detect the activity of nerve cells that control muscles through electromyography (EMG).

Figure 3:
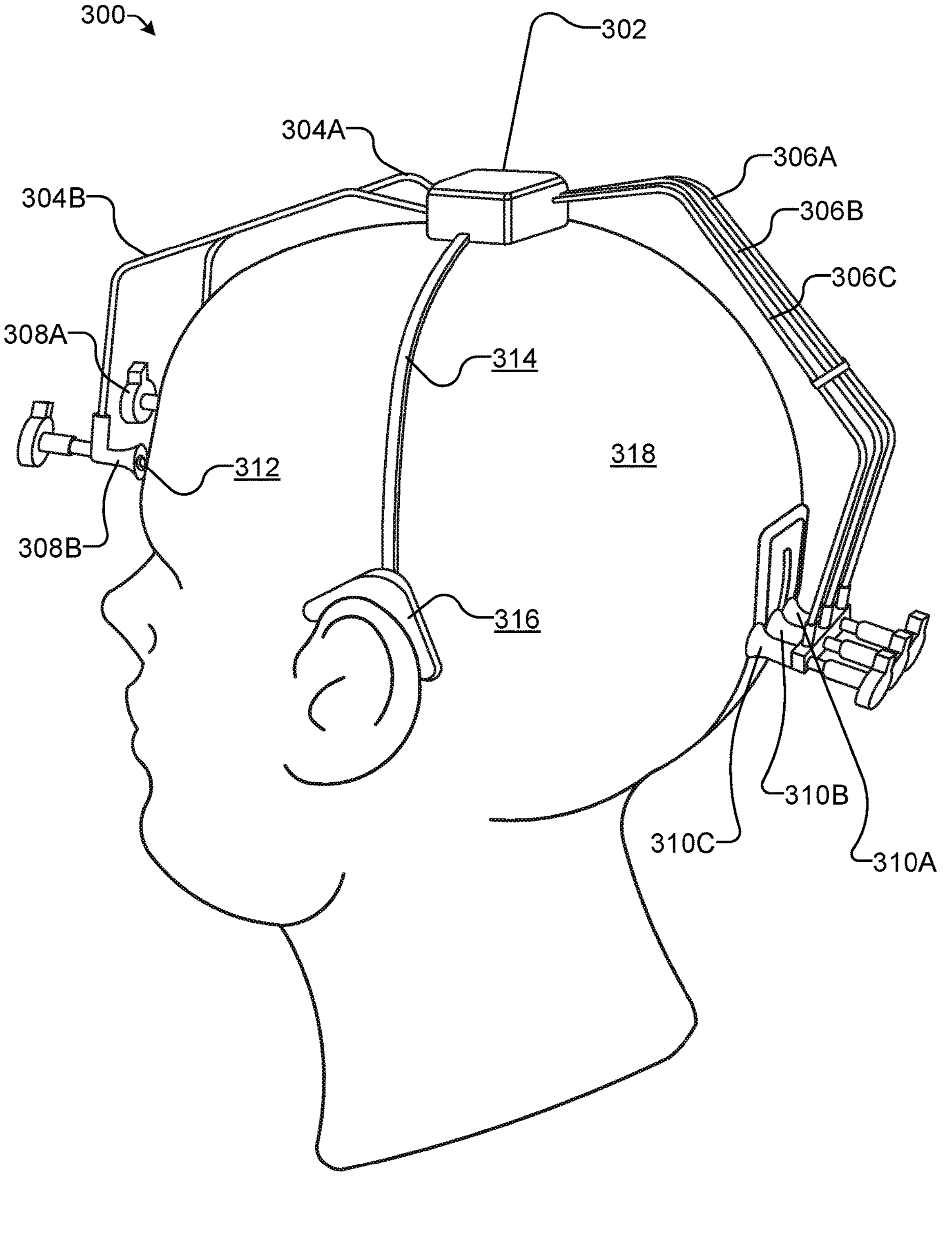
FIG. 3 is a diagram of an EEG headset worn by a user.

FIG. 3 shows a configuration of a mobile EEG headset 300. The EEG headset 300 may, but does not necessarily, include electrodes shaped like the electrode 100 shown in FIG. 1 and spring-loaded electrode holders 200 such as those shown in FIG. 2.

A housing unit 302 is configured to be positioned on the top of the head 318 of a user. The housing unit 302 may contain various electronics used in EEG headsets such as an amplifier, an analog to digital converter, and/or a wireless communication module. The housing unit 302 also provides a point of attachment for multiple arms 304, 306 with curved configurations that hold electrodes in contact with the head 318. Although five separate arms 304A, 304B, 306A-C are shown in this illustrative configuration, the EEG headset 300 may include a greater or lesser number of arms. Each of the arms 304, 306 has a shape, dimension, and curvature that secures an electrode in contact with the head of the user with a specific amount of force. Thus, the arms 304, 306 themselves behave as springs flexibly maintaining contact between electrodes and the head 318 of the user. When a user puts on the EEG headset 300 from the top of their head, the electrodes will naturally penetrate the hair layer and contact the scalp.

The arms 304, 306 may extend from the housing unit 302 to contact multiple different regions of the head 318 of the user. In this illustrative design, two arms 304A, 304B position electrodes in contact with the forehead or frontal region of the head 318. Three arms 306A, 306B, 306C position electrodes in contact with the rear or occipital region of the head 318. Other configurations are also possible such as arms that position electrodes in contact with the sides of the head of the user. One possible configuration includes arms that position electrodes in contact with the front, back, right side, and left side of the head 318 of the user. Another possible configuration includes arms radiating from the housing unit 302 in multiple directions so that electrodes contact the head 318 of the user around its entire circumference. When configured such that arms extend to at least two opposite sides of the head 318, such as the front and back or the left and right side, opposing force from the at least two sets of arms may serve to hold the EEG headset 300 in place.

The end of each arm 304, 306 distal from the housing unit 302 may have a spring-loaded electrode holder 308A-B, 310A-C is configured to maintain electrode in contact with the head 318 of the user with a consistent amount of force. The spring-loaded electrode holders 308, 310 may be the same or similar to the spring-loaded electrode holder shown in FIG. 2. However, each arm 304, 306 may simply have an electrode on the end without a spring-loaded electrode holder. Each spring-loaded electrode holder 308, 310 includes an electrode 312 which is visible in this view only for spring-loaded electrode holder 308B.

The amount of force with which the arms 304, 306 position electrodes in contact with the head 318 of the user may vary depending on the region of the head 318. For example, a first set of arms 304A and 304B may be configured to position electrodes in contact with a first region of the head 318 such as the frontal region. An amount of pressure that is not uncomfortable for most users when applied to the frontal region is about 350-450 g/cm$^2$ such as about 400 g/cm$^2$. Thus, the first set of arms 304A and 304B may be curved in a configuration that positions electrodes in contact with the frontal region with about 350-450 g/cm$^2$ of pressure. Similarly, the second set of arms 306A-C may be configured to position electrodes in contact with a second region of the head 318 such as the occipital region. An amount of pressure that is not uncomfortable for most users when applied to the occipital region is about 550-650 g/cm$^2$ such as about 600 g/cm$^2$. Thus, the second set of arms 306A-C may be curved in a configuration that positions electrodes in contact with the frontal region with about 550-650 g/cm$^2$ of pressure.

However, different users have different sided and shaped heads 318. The EEG headset 300 built to a particular size will have a tighter or looser fit depending on the size and shape of the user's head 118. The relative size of the user's head 118 will thus affect the amount of pressure that the arms 304, 306 contact the head 118. In some configurations, the amount of pressure may be adjusted by bending the arms 304, 306 or adjusting the angle of connection with the housing unit 302. In some configurations, the spring-loaded electrode holders 308, 310 accommodate different sized heads 318 while maintaining the same amount of pressure between the electrodes and the scalp.

The EEG headset 300 may also include a stabilizing band 314 connected to the housing unit 302 and configured to extend across the head 318 of the user. In this example configuration in which the arms 304, 306 extend to the front and back of the head 318 of the user, the stabilizing band 314 extends laterally across the head of the user from the left ear to the right ear. The stabilizing band 314 may include ear rests 316 that sit on top of the ears of the user and support the EEG headset 300. In an alternative configuration where the arms 304, 306 extend laterally across the head 318 of the user, the stabilizing band 314 may extend lengthwise from the front of the head to the back of the head.

Figure 4:
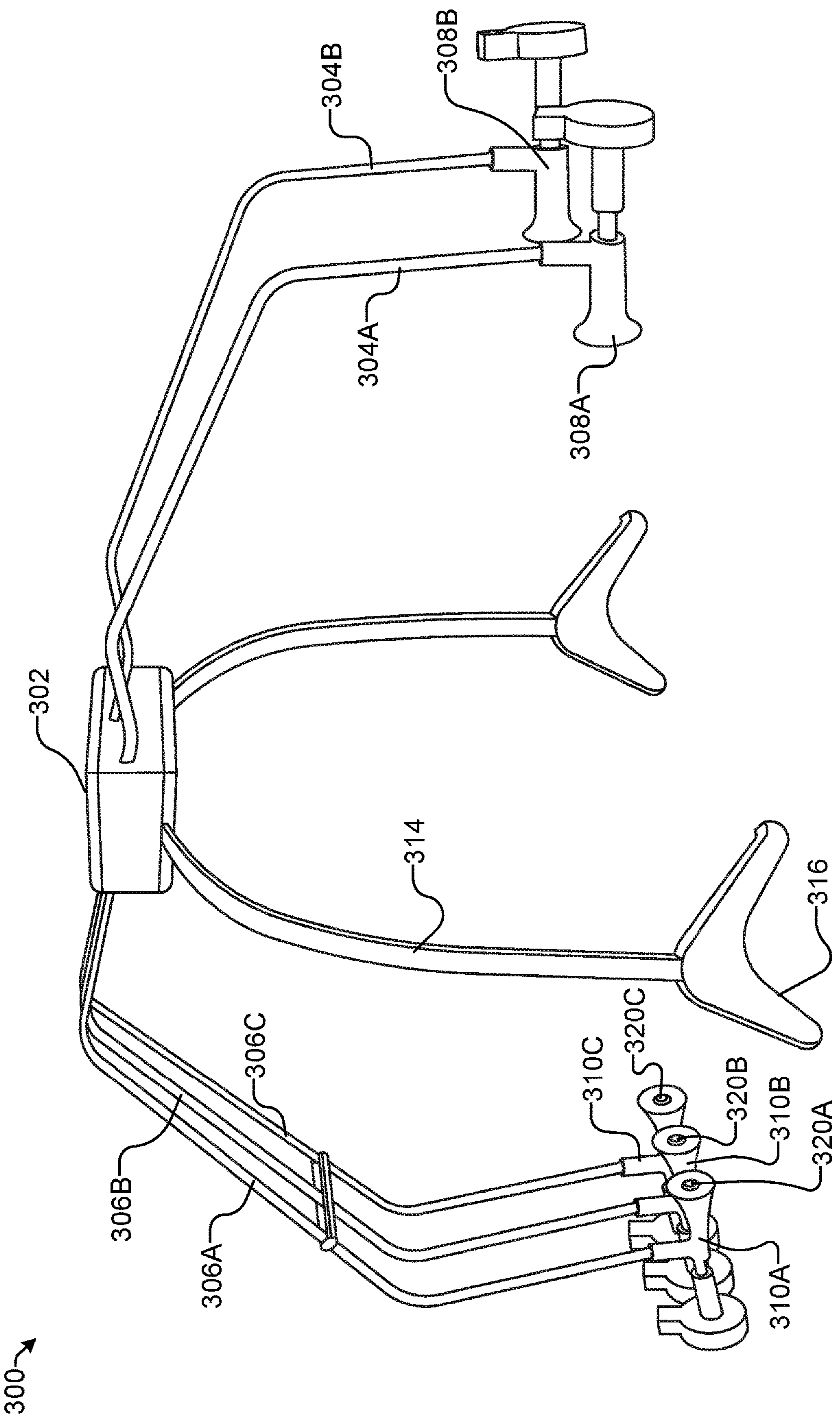
FIG. 4 is a different view of the EEG headset of FIG. 3.

FIG. 4 shows an alternative view of the EEG headset 300. This view shows the EEG headset 300 without the head 318 of the user. This view shows that a first set of arms 304A, 304B are both connected to the same side of the housing unit 302. Similarly, a second set of arms 306A-C extends from a different side of the housing unit 302. Also, electrodes 320A-C in the spring-loaded electrode holders 310A-C are visible in this view. This design for an EEG headset 300 is easy to wear because the arms 304, 306 are thin and light which removes unnecessary weight. Users can wear this type of EEG headset 300 themselves without the assistance of a skilled technician. Thus, it is suitable for a broader range of applications than medical diagnosis or research. For example, the EEG headset 300 may be integrated or combined with other wearable devices such as a head-mounted display (HMD) that provides a virtual reality, an augmented reality, or a mixed reality interface.

Additionally, when configured with spring-loaded electrode holders 308, 310, the force by which each electrode is maintained in contact with the head 318 of the user is modulated by two springs. The first is the spring provided by the respective arm 304, 306 and the second is the spring included in the spring-loaded electrode holder 308, 310. This maintains a consistent and comfortable amount of force between the electrode and the scalp of the user. Additionally, when the tips of the electrodes are shaped as hemispheres this alleviates scratching and discomfort when the position of the electrodes shift. Thus, users may be able to wear the EEG headset 300 comfortably for extended periods of time while engaged in typical daily activities.

Figure 5:
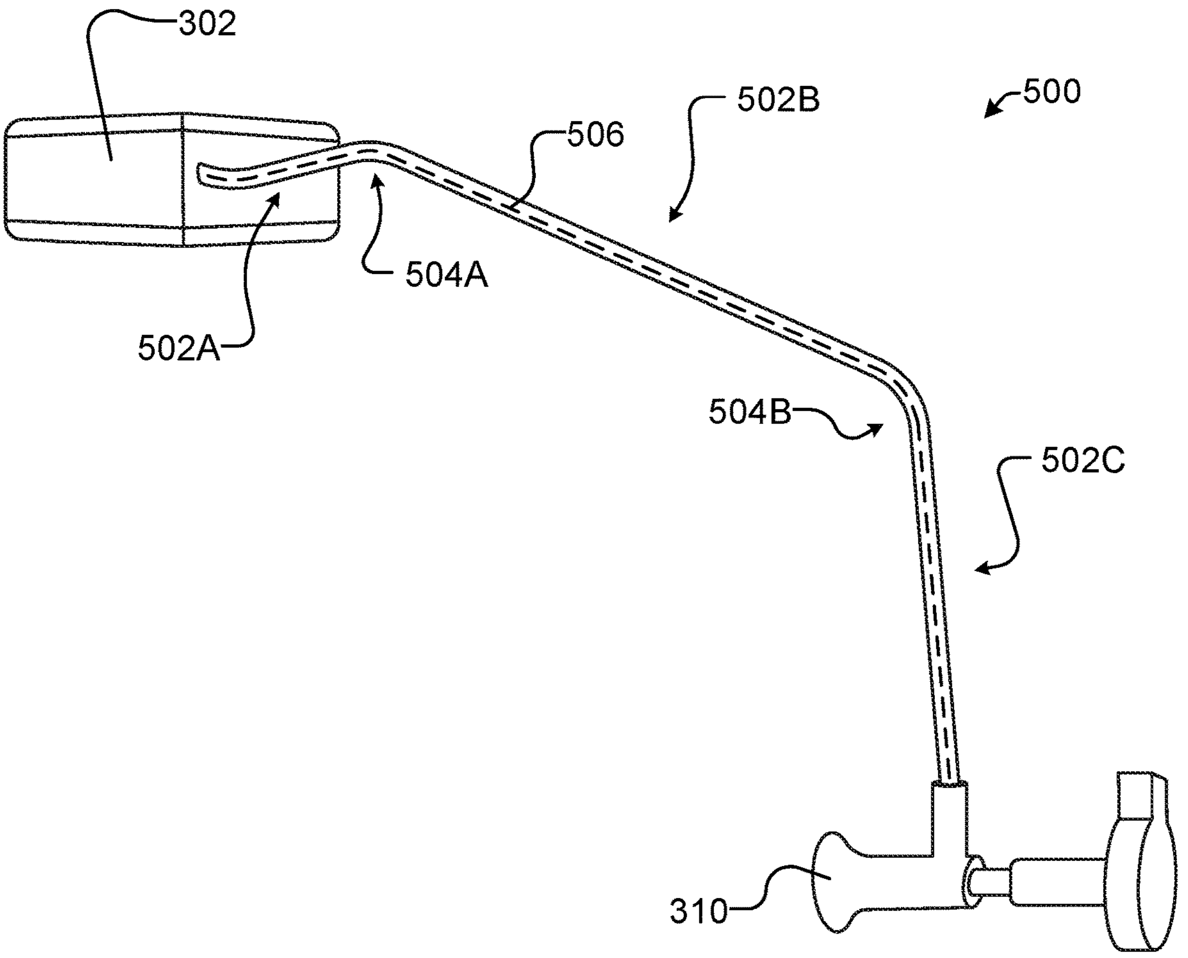
FIG. 5 is a diagram showing an illustrative configuration of an arm of the EEG headset of FIG. 3.

FIG. 5 shows a single arm 500 of the EEG headset 300. In this configuration, curvature of the arm 500 is provided by a plurality of straight regions 502A-C connected by curved regions 504A, 504B. The respective lengths of the straight regions 502A-C and the extent of curvature of the curved regions 504A, 504B define the overall shape and curvature of the arm 500. These dimensions together with the flexibility of the arm 500 determine the amount of force with which the arm 500 maintains an electrode in contact with the head of a user.

In some implementations, the arm 500 may be hollow. One or more wires 506 may be routed through the hollow body of the arm 500. The wire 506 may provide a conductive connection between the electrode on the end of the arm 500 and the housing unit 302.

Figure 6:
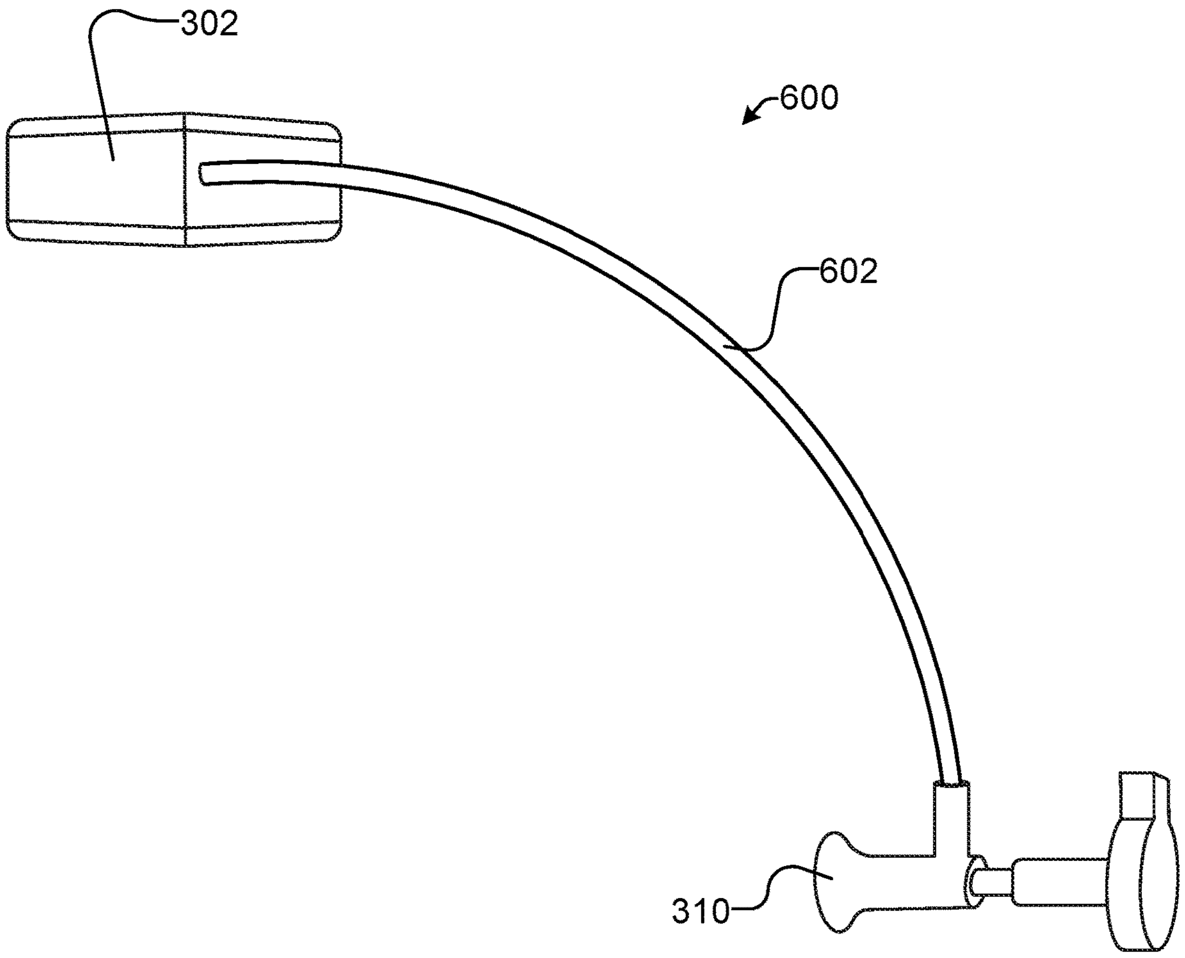
FIG. 6 is a diagram showing an illustrative configuration of an arm of the EEG headset of FIG. 3.

FIG. 6 shows an alternative configuration for a single arm 600 of the EEG headset 300. In this example configuration, the arm 600 is a continuous smooth curve 602 from the spring-loaded electrode holder 310 or electrode at the end of the arm 600 to the housing unit 302. This arm 600 may also be hollow. The length of the arm 600, the extent of curvature of the smooth curve 602, and the flexibility of the arm 600 determine the amount of force with which the arm 600 maintains an electrode in contact with the head of a user. Other shapes and configurations for the arms are also possible besides straight regions interspersed with curved regions or continuous smooth curves.

Figure 7:
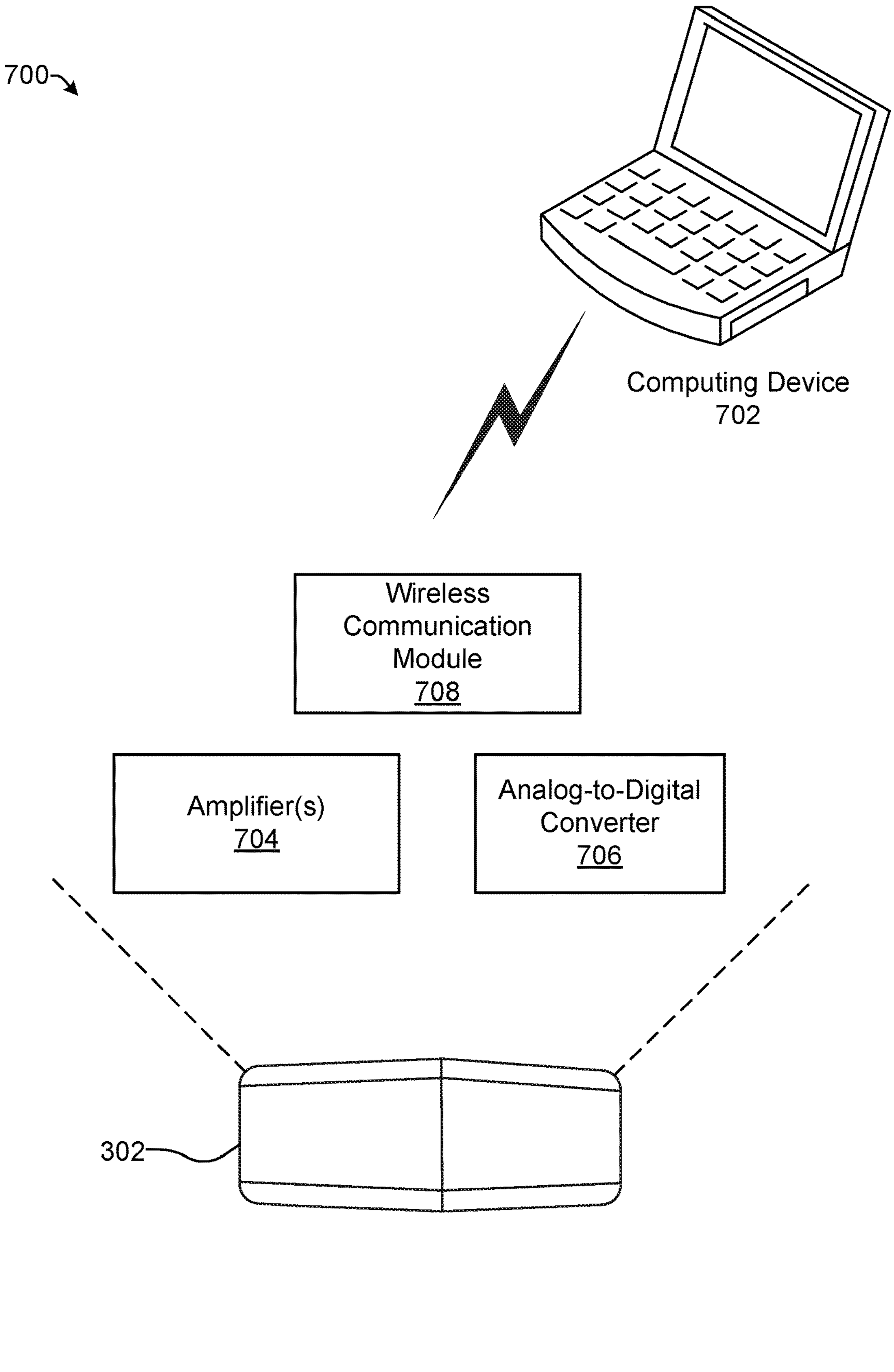
FIG. 7 is a schematic diagram illustrating electronic components of an EEG headset in communication with a computing device.

FIG. 7 is a schematic diagram 700 showing electronic components of an EEG headset in communication with a computing device 702. For the sake of simplicity, elements of the EEG headset other than the housing unit 302 are omitted from FIG. 7. The housing unit 302 may contain electronics and a power source for the EEG headset. Selection, configuration, and design of electronics used in EEG headsets are known to those of ordinary skill in the art.

Electronics that may be included in the housing unit 302 can include one or more amplifiers 704, an analog-to-digital converter 706, and a wireless communication module 708. The amplifier(s) 704 may be any of an instrument amplifier, an operation amplifier, and/or a bio-signal amplifier. An instrumentation amplifier is a type of differential amplifier that has been outfitted with input buffer amplifiers, which eliminate the need for input impedance matching and thus make the amplifier particularly suitable for use in measurement equipment. An operation amplifier is a DC-coupled high-gain electronic voltage amplifier with a differential input and, usually, a single-ended output. A bio-signal amplifier is an electrophysiological device used to gather and increase the signal integrity of physiologic electrical activity for output to various sources. Any of these amplifiers may include one or more integrated circuits. The housing unit 302 may include multiple amplifiers of the same or different type.

Signals from the electrodes of the EEG headset received at the amplifier 704 may be in the range of about 10 $\mu$V to 100 $\mu$V, over the frequency range of about 0.1-100 Hz. The amplifier 704 amplifies the voltage between an active electrode and a reference electrode. Depending on the type of amplifier this may provide 1,000-100,000 times or 60-100 dB of voltage gain. The housing unit 302 may also include a filter to band-pass filter the amplified EEG signal. The amplified signal may then be digitized via the analog-to-digital converter 706, after being passed through an anti-aliasing filter. Analog-to-digital sampling is typically performed at about 128-1024 Hz in clinical scalp EEG; however, sampling rates of up to 20 kHz may be used. A microcontroller (not shown) in communication with the analog-to-digital converter 706 may function to control the generation of a digital EEG signal.

The computing device 702 is communicatively connected to the EEG headset. Amplified signals from the amplifier 704 may be communicated wirelessly to the computing device 702 by the wireless communication module 708. For example, the wireless communication module 708 may use radio waves such as Bluetooth® to transmit signals to the computing device 702. Alternatively, there may be a wired connection (not shown) between the housing unit 302 and the computing device 702. The computing device 702 may be a portable computing device, a hand-held computing device, a wearable computing device, or a different kind of computing device. For example, the computing device 702 may be a smartphone, tablet, laptop, or desktop computer. In some implementations, the computing device 702 or a different computing device may be integrated into the EEG headset.

The computing device 702 may include EEG software configured to process signals received from the wireless communication module 708 such as EEGLAB (Delorme, Arnaud; Makeig, Scott (2004). "EEGLAB: an open source toolbox for analysis of single-trial EEG dynamics including independent component analysis". *Journal of Neuroscience Methods*. Elsevier BV. 134 (1): 9-21.) or the Neurophysiological Biomarker Toolbox (available from www.poil.dk/s/nbt-v0-5-1-alpha/874#. VIzD-qbEht1).

Signals received by the computing device 702 may also be used as user input to create a BCI between the EEG headset and the computing device 702. In some implementations, the computing device 702 may have specialized hardware such as OpenBCI which is an open-source brain-computer interface platform (see openbci.com). Additional applications besides conventional EEG and BCI include, but are not limited to, monitoring of the brain state (cognitive load, stress, attention, fatigue due to long hours of working) and monitoring of biological wellbeing.

Figure 8:
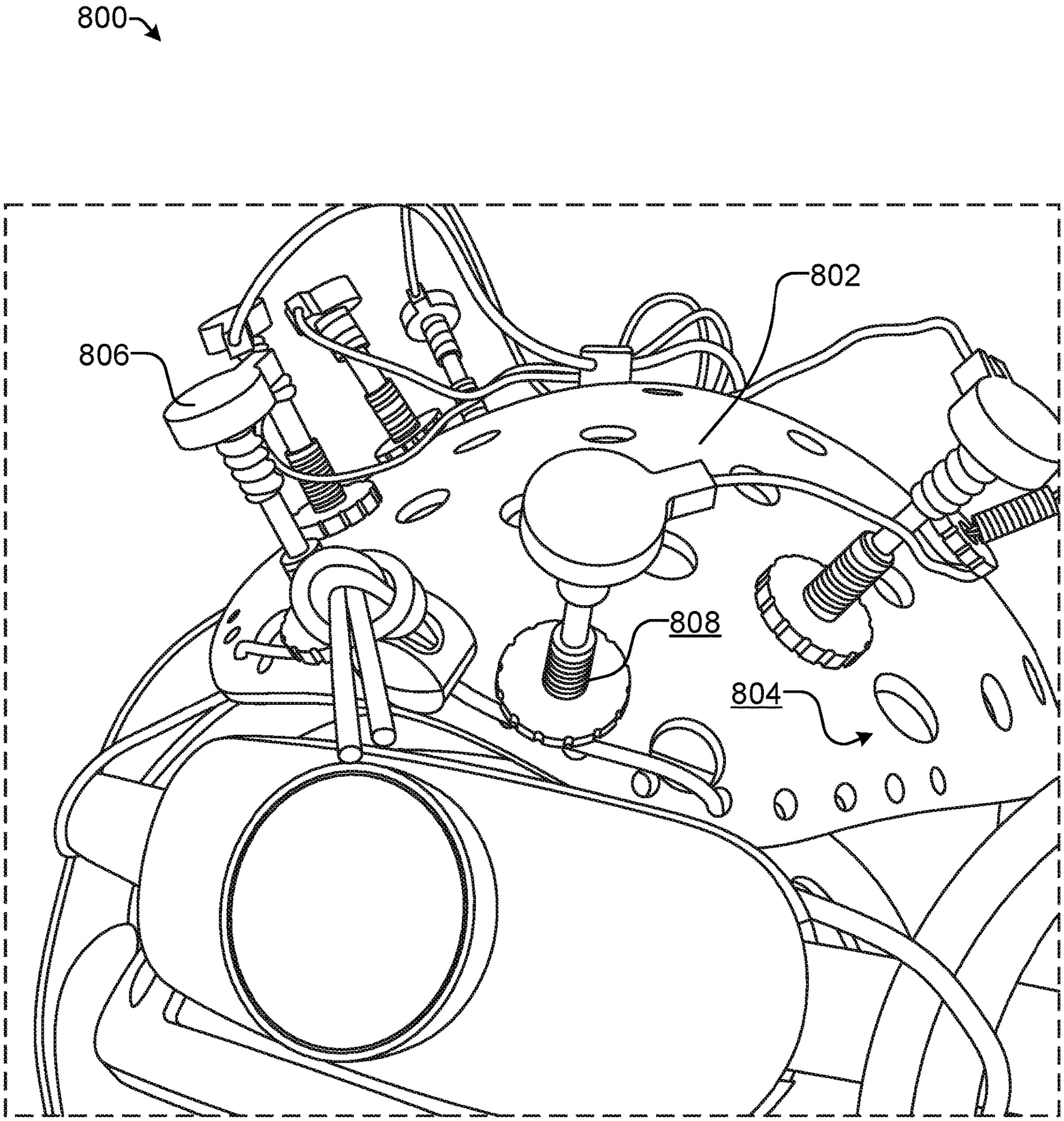
FIG. 8 is a diagram of an alternative configuration of an EEG headset.

FIG. 8 is diagram 800 illustrating an alternative configuration for an EEG headset. In this configuration, a wearable cap 802 configured to be placed on the head of a user contains a plurality of holes 804 into which electrode holders 806 may be inserted. Thus, electrodes may be added or removed from the wearable cap 802 by addition or removal of an electrode holder 806 in any of the respective holes 804. The electrode holders 806 may be the same or similar to the electrode holder 200 shown in FIG. 2. Thus, the electrode holders 806 may be implemented as spring-loaded electrode holders. The amount of force generated by a spring in one of the electrode holders 806 may be based on the location on the head of the user contacted by the electrode.

The depth of electrodes relative to the wearable cap 802 may be adjusted by height adjustment mechanisms 808 that control the extent to which an electrode holder 806 penetrates through the wearable cap 802. In an implementation, the height adjustment mechanisms 808 may be implemented by threads that may be rotated to adjust the height of an electrode holder 806. The height of each electrode holder 806 may be adjusted to provide a balance between conductivity between the electrode and the user's scalp and comfort. If implemented as spring-loaded electrode holders, excess force may be absorbed by the springs and reduce discomfort.

Electrodes in any of the EEG headsets described in this disclosure may continuously measure electrical potentials in the user's brain at millisecond intervals. The EEG headset may include multiple recording electrodes, a ground electrode, and a reference electrode which enable measurement of the frequency of electrical potentials of brain activity. The EEG headset is configured to enable the characterization of brain activity from one or more regions of the user's brain through a non-invasive method. Specifically, each of the one or more recording electrodes forms a channel with a reference electrode. Each channel represents the difference in measured electrical potential between the corresponding recording electrode and the reference electrode. The ground electrode is connected to the circuit formed by the recording electrodes and reference electrode such that electrical signals are filtered out from sources other than the user's brain, such as power line noise. The recording electrodes are positioned on the wearable interface such that they receive potential signals generated at the user's brain.

The EEG headset may be used as an EEG monitoring device to measure brain activity for an EEG system. Additionally, or alternatively, the EEG headset may be used to transform brain activity into computer input thereby creating a BCI. The wearable cap 802 may be connected through wireless or wired connection to a computing device. In some implementations, the computing device is a wearable computing device. For example, the wearable computing device may be an HMD such as a virtual reality, an augmented reality, or a mixed reality headset.

Figure 9:
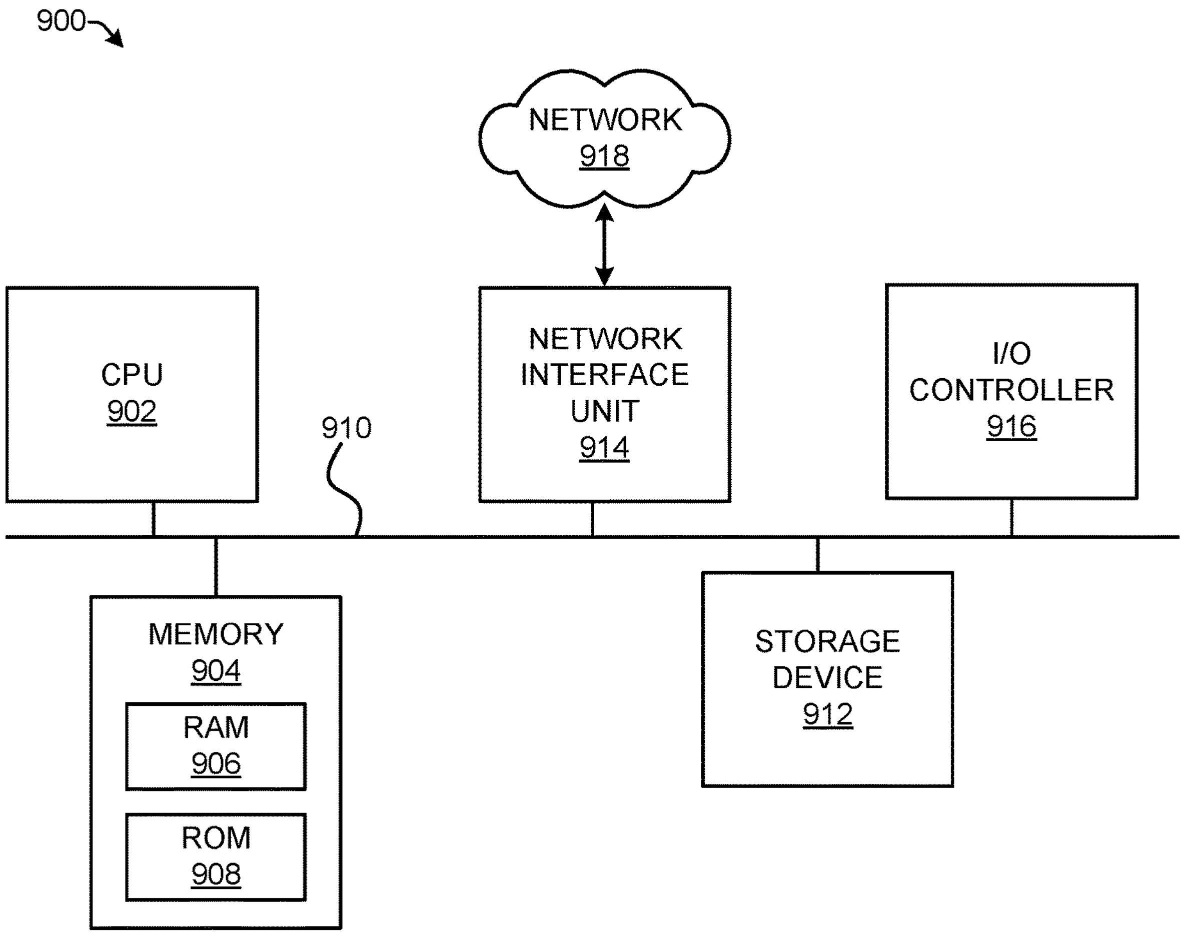
FIG. 9 is a computer architecture diagram illustrating a computing device architecture for a computing device capable of implementing aspects of the techniques and technologies presented herein.

FIG. 9 shows details of an example computer architecture for a computer capable of executing the techniques disclosed herein. Thus, the computer architecture 900 illustrated in FIG. 9 illustrates an architecture for a portable device, a hand-held device, a wearable device, a desktop device, or network accessible computer, or any other types of computing devices suitable for implementing the functionality described herein. Examples of portable devices include, but are not limited to, laptop computers, notebook computers, tablets, and vehicle-mounted computing devices. Examples of hand-held devices include, but are not limited to, smartphones and media players. Examples of wearable devices include, but are not limited to, smartwatches, activity bands, glasses, headphones, earbuds, and HMDs. Examples of network accessible computers include, but are not limited to, server computers and cloud computing systems. The computer architecture 900 may be utilized to execute any aspects of the computer readable instructions presented herein.

The computer architecture 900 illustrated in FIG. 9 includes a central processing unit 902 ("CPU"), a system memory 904, including a random-access memory 906 ("RAM") and a read-only memory ("ROM") 908, a system bus 910 that couples the memory 904 to the CPU 902, and a storage device 912. A basic input/output system containing the basic routines that help to transfer information between elements within the computer architecture 900, such as during startup, is stored in the ROM 908.

Communication media includes computer readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

By way of example, and not limitation, computer storage media may include volatile and non-volatile, removable and non-removable media implemented in any method or technology for storage of information such as computer-readable instructions, data structures, program modules, or other data. For example, computer media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information, and which can be accessed by the computer architecture 900. For purposes of the claims, the phrase "computer storage medium," "computer-readable storage medium," or "computer-readable medium," and variations thereof, does not include waves, signals, and/or other transitory and/or intangible communication media, per se.

According to various techniques, the computer architecture 900 may operate in a networked environment using logical connections to remote computers through a network 918 and/or another network (not shown). The computer architecture 900 may connect to the network 918 through a network interface unit 914 connected to the bus 910. It should be appreciated that the network interface unit 914 also may be utilized to connect to other types of networks and remote computer systems. The computer architecture 900 also may include an input/output controller 916 for receiving and processing input from a number of other devices, including a keyboard, mouse, or electronic stylus (not shown in FIG. 9). Similarly, the input/output controller 916 may provide output to a display screen, a printer, or other type of output device (also not shown in FIG. 9).

It should be appreciated that the computer readable instructions described herein may, when loaded into the CPU 902 and executed, transform the CPU 902 and the overall computer architecture 900 from a general-purpose computing system into a special-purpose computing system customized to facilitate the functionality presented herein. The CPU 902 may be constructed from any number of transistors or other discrete circuit elements, which may individually or collectively assume any number of states. More specifically, the CPU 902 may operate as a finite-state machine, in response to computer readable instructions disclosed herein. These computer-executable instructions may transform the CPU 902 by specifying how the CPU 902 transitions between states, thereby transforming the transistors or other discrete hardware elements constituting the CPU 902.

Encoding the computer readable instructions presented herein also may transform the physical structure of the computer-readable media presented herein. The specific transformation of physical structure may depend on various factors, in different implementations of this description. Examples of such factors may include, but are not limited to, the technology used to implement the computer-readable media, whether the computer-readable media is characterized as primary or secondary storage, and the like. For example, if the computer-readable media is implemented as semiconductor-based memory, the computer readable instructions disclosed herein may be encoded on the computer-readable media by transforming the physical state of the semiconductor memory. For example, the computer readable instructions may transform the state of transistors, capacitors, or other discrete circuit elements constituting the semiconductor memory. The computer readable instructions also may transform the physical state of such components in order to store data thereupon.

As another example, the computer-readable media disclosed herein may be implemented using magnetic or optical technology. In such implementations, the computer readable instructions presented herein may transform the physical state of magnetic or optical media, when the computer readable instructions are encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer architecture 900 in order to store and execute the computer readable instructions presented herein. It also should be appreciated that the computer architecture 900 may include other types of computing devices, including hand-held computers, embedded computer systems, personal digital assistants, and other types of computing devices known to those skilled in the art. It is also contemplated that the computer architecture 900 may not include all of the components shown in FIG. 9, may include other components that are not explicitly shown in FIG. 9, or may utilize an architecture completely different than that shown in FIG. 9.

ILLUSTRATIVE IMPLEMENTATIONS

The following clauses described multiple possible implementations for implementing the features described in this disclosure. The various implementations described herein are not limiting nor is every feature from any given implementation required to be present in another implementation. Any two or more of the implementations may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. In an implementation, this disclosure provides an electroencephalographic (EEG) headset (300) comprising: a housing unit (302) configured to be positioned on the top of a head of a user; a first arm (304) connected to the housing unit and having a first electrode (312) on an end, the first arm curved in a configuration that positions the first electrode in contact with a first region of the head (318) of the user with a first amount of force; and a second arm (306) connected to the housing unit and having a second electrode (320) on an end, the second arm curved in a configuration that positions the second electrode in contact with a second region of the head of the user with a second amount of force. Advantages of this implementation include increased user comfort while maintaining a constant amount of force between electrodes and the scalp of a user.

Clause 2. In an implementation, this disclosure provides the EEG headset of clause 1, wherein the first arm has a continuous smooth curve (602) from the housing unit to the first electrode.

Clause 3. In an implementation, this disclosure provides the EEG headset of clause 1, wherein the first arm has a plurality of straight regions (502) connected by curved regions (504).

Clause 4. In an implementation, this disclosure provides the EEG headset of any of clauses 1-3, wherein the first arm is hollow and contains a wire (506) extending from the first electrode to the housing unit. This implementation provides an advantage of protecting the wire by enclosing it in inside the hollow arm and a simpler and cleaner appearance of the EEG headset.

Clause 5. In an implementation, this disclosure provides the EEG headset of any of clauses 1-4, wherein the first region of the head of the user is the frontal region and the second region of the head of the user is the occipital region. This implementation provides an advantage of detecting brain activity at both the front and rear of the head.

Clause 6. In an implementation, this disclosure provides the EEG headset of clause 5, wherein the first amount of pressure is about 350-450 $g/cm^2$ and the second amount of pressure is about 550-650 $g/cm^2$. This implementation provides an advantage of maintaining electrodes in contact with the scalp of the user with an amount of pressure that is comfortable and creates good conductance between the electrodes and the user's scalp.

Clause 7. In an implementation, this disclosure provides the EEG headset of any of clauses 1-6, wherein the first electrode comprises a spring-loaded electrode holder (308) configured maintain the first electrode (312) in contact with the first region of the head of the user with a consistent amount of force and the second electrode comprises a spring-loaded electrode holder (310) configured to maintain the second electrode in contact with the second region of the head of the user with a consistent amount of force. This implementation provides an advantage of additional springs in the spring-loaded electrode holders that work together with the curved arms to regulate the amount of pressure with which the electrodes contact the head of the user.

Clause 8. In an implementation, this disclosure provides the EEG headset of clause 7, wherein a spring in the spring-loaded electrode holder of the first electrode is configured maintain the first electrode in contact with the first region of the head of the user with about 350-450 $g/cm^2$ of pressure and a spring in the spring-loaded electrode holder of the second electrode is configured maintain the second electrode in contact with the second region of the head of the user with about 550-650 $g/cm^2$ of pressure. This implementation provides an advantage of providing an amount of force for electrodes that is adapted to and comfortable for specific regions on the head of the user.

Clause 9. In an implementation, this disclosure provides the EEG headset of any of clauses 1-8, wherein the housing unit contains at least one of an amplifier (704), an analog-to-digital converter (706), or a wireless communication module (708). This implementation provides an advantage of including placing electronics for the EEG headset in a location of the top of the user's head that comfortably supports the weight of the electronics.

Clause 10. In an implementation, this disclosure provides the EEG headset of any of clauses 1-9, further comprising a stabilizing band (314) connected to the housing unit and configured to extend across the head of the user. This implementation provides the advantage of stabilizing the EEG headset on the head of the user.

Clause 11. In an implementation, this disclosure provides a system configured to implement a brain-computer interface (BCI) comprising: the EEG headset of any of clauses 1-10, wherein the housing unit (302) comprises a wireless communication module (708); and a computing device (702) communicatively connected to the wireless communication module and configured to process signals received from the EEG headset as user input. This implementation provides an advantage of increased comfort for the user of a BCI.

Clause 12. In an implementation, this disclosure provides the system of clause 11, wherein the EEG headset comprises: at least one additional arm (304B) connected to a same side of the housing unit as the first arm (304A), having an electrode on an end, and configured to position the electrode in contact with the first region of the head (318) of the user with the first amount of force; and at least one additional arm (306B, 306C) connected to a same side of the housing unit as the second arm (306A), having an electrode on an end, and configured to position the electrode in contact with the second region of the head of the user with the second amount of force. This implementation provides an advantage of additional electrodes to detect electrical signals from multiple locations of the head of the user.

Clause 13. In an implementation, this disclosure provides the a spring-loaded electrode holder (200) comprising: an electrode (100) formed from a conductive material; a spring (202) connected to the electrode (100) and configured to maintain the electrode (100) in contact with the skin of a user with a consistent amount of force; an interface (206) connected to the spring (202) and configured to form a conductive connection to the spring-loaded electrode holder; and a conductive connection between the electrode and the interface. This implementation provides an advantage of adsorbing excess force and regulating the amount of force with which an electrode contacts the skin of a user.

Clause 14. In an implementation, this disclosure provides the spring-loaded electrode holder of clause 13, further comprising a housing (204) configured to encase the spring. This provides an advantage of rigidity and protection of the spring in the spring-loaded electrode holder.

Clause 15. In an implementation, this disclosure provides the spring-loaded electrode holder of clause 13 or 14, wherein the spring comprises a coil spring.

Clause 16. In an implementation, this disclosure provides the spring-loaded electrode holder of any of clauses 13-15, wherein the electrode has a hemispherical shaped tip. This implementation provides an advantage of increased user comfort as compared to a pointed electrode tip.

Clause 17. In an implementation, this disclosure provides the spring-loaded electrode holder of clause 16, wherein a diameter of the hemispherical shaped tip is about 1.5-2.5 mm, about 1.5 mm, about 2.0 mm, or about 2.5 mm. This implementation provides the advantage of an electrode tip size that can be readily manufacture and also easily penetrate between the hair on the scalp of a user.

Clause 18. In an implementation, this disclosure provides the spring-loaded electrode holder of any of clauses 13-17, wherein the conductive material is silver/sliver chloride. This implementation provides an advantage of a conductive material that is well suited for an EEG electrode.

Clause 19. In an implementation, this disclosure provides the spring-loaded electrode holder of any of clauses 13-18, further comprising a wire (208) connected to the electrode and the interface and wherein the conductive connection between the electrode and the interface comprises the wire. This implementation provides the advantage of creating a conductive connection between the electrode and other components connected to the spring-loaded electrode holder.

Clause 20. In an implementation, this disclosure provides the spring-loaded electrode holder of any of clauses 13-19, wherein the conductive connection between the electrode and the interface comprises the spring. This implementation provides the advantage of creating a conductive connection between the electrode and other components connected to the spring-loaded electrode holder without using additional wires or material.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context.

It should be appreciated that any reference to "first," "second," etc. users or other elements within the Summary and/or Detailed Description is not intended to and should not be construed to necessarily correspond to any reference of "first," "second," etc. elements of the claims. Rather, any use of "first" and "second" within the Summary, Detailed Description, and/or claims may be used to distinguish between two different instances of the same element (e.g., two different users, two different electrodes, etc.).

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

All patents, patent applications, and references mentioned herein are fully incorporated by reference.

The invention claimed is:

1. An electroencephalographic (EEG) headset comprising:

a housing unit configured to be positioned on the top of a head of a user;

a first arm connected to the housing unit and having a first electrode on an end, wherein the first arm is configured to hold the first electrode in contact with a first region of the head of the user with a first amount of force due to a curvature of the first arm, the first arm has at least one straight region and the first arm has at least one straight and at least one curved region between the housing unit and the first electrode at least one curved region between the housing unit and the first electrode, and the first arm is not in direct contact with the head of the user; and a second arm connected to the housing unit and having a second electrode on an end, wherein the second arm is configured to hold the second electrode in contact with a second region of the head of the user with a second amount of force greater than the first amount of force due to a curvature of the second arm, the second arm has at least one straight region and/or at least one curved region between the housing unit and the second electrode, and the second arm is not in direct contact with the head of the user.

2. The EEG headset of claim 1, wherein the first arm is hollow and contains a wire extending from the first electrode to the housing unit.

3. The EEG headset of claim 1, wherein the first region of the head of the user is the frontal region and the second region of the head of the user is the occipital region.

4. The EEG headset of claim 3, wherein the first amount of force is about 350-450 g/cm$^2$ and the second amount of force is about 550-650 g/cm$^2$.

5. The EEG headset of claim 1, wherein the first electrode comprises a spring-loaded electrode holder configured maintain the first electrode in contact with the first region of the head of the user with a consistent amount of force and the second electrode comprises a spring-loaded electrode holder configured to maintain the second electrode in contact with the second region of the head of the user with a consistent amount of force.

6. The EEG headset of claim 5, wherein a spring in the spring-loaded electrode holder of the first electrode is configured maintain the first electrode in contact with the first region of the head of the user in conjunction with force provided by the first arm with about 350-450 g/cm$^2$ of force and a spring in the spring-loaded electrode holder of the second electrode is configured maintain the second electrode in contact with the second region of the head of the user in conjunction with force provided by the second arm with about 550-650 g/cm$^2$ of force.

7. The EEG headset of claim 1, wherein the housing unit contains at least one of an amplifier, an analog-to-digital converter, or a wireless communication module.

8. The EEG headset of claim 1, further comprising a stabilizing band connected to the housing unit and configured to extend across the head of the user.

9. A system configured to implement a brain-computer interface (BCI) comprising:

the EEG headset of claim 1, wherein the housing unit comprises a wireless communication module; and a computing device communicatively connected to the wireless communication module and configured to process signals received from the EEG headset via user input.

10. The system of claim 9, wherein the EEG headset comprises:

at least one additional arm connected to a same side of the housing unit as the first arm, having an electrode on an end, and configured to position the electrode in contact with the first region of the head of the user with the first amount of force; and at least one additional arm connected to a same side of the housing unit as the second arm, having an electrode on an end, and configured to position the electrode in contact with the second region of the head of the user with the second amount of force.

11. The EEG headset of claim 1, further comprising a spring-loaded electrode holder comprising:

the first electrode formed from a conductive material;

a spring connected to the first electrode and configured to maintain the first electrode in contact with the skin of the user with a consistent amount of force;

an interface connected to the spring and configured to form a conductive connection between the spring-loaded electrode holder and an external circuit; and a conductive path between the first electrode and the interface, the conductive path comprising either (i) a wire connected to the first electrode and to the interface or (ii) the spring.

12. The EEG headset of claim 11, wherein the spring-loaded electrode holder further comprises a housing configured to encase the spring.

13. The EEG headset of claim 11, wherein the spring comprises a coil spring.

14. The EEG headset of claim 11, wherein the first electrode has a hemispherical shaped tip.

15. An electroencephalographic (EEG) headset comprising:

a housing unit configured to be positioned on the top of a head of a user;

a first arm connected to the housing unit and having a first spring-loaded electrode holder on an end, the first spring-loaded electrode holder comprising a first electrode formed from a conductive material, a spring connected to the first electrode and configured to maintain the first electrode in contact with the skin of the user with a consistent amount of force, an interface connected to the spring and configured to form a conductive connection between the spring-loaded electrode holder and the housing unit, and a conductive path between the first electrode and the interface, wherein the first arm is configured to hold the first electrode in contact with a first region of the head of the user with a first amount of force due to a curvature of the first arm, the first arm has at least one straight region and the first arm has at least one straight and at least one curved region between the housing unit and the first electrode at least one curved region between the housing unit and the first electrode, and the first arm is not in direct contact with the head of the user; and a second arm connected to the housing unit and having a second spring-loaded electrode holder on an end, the second spring-loaded electrode holder comprising a second electrode formed from a conductive material, a spring connected to the second electrode and configured to maintain the second electrode in contact with the skin of the user with a consistent amount of force, an interface connected to the spring and configured to form a conductive connection between the spring-loaded electrode holder and the housing unit, and a conductive path between the second electrode and the interface, wherein the second arm is configured to hold the second electrode in contact with a second region of the head of the user with a second amount of force greater than the first amount of force due to a curvature of the second arm, the second arm has at least one straight region and/or at least one curved region between the housing unit and the second electrode, and the second arm is not in direct contact with the head of the user.

16. A system configured to implement a brain-computer interface (BCI) comprising:

the EEG headset of claim 15, wherein the housing unit comprises a wireless communication module; and a computing device communicatively connected to the wireless communication module and configured to process signals received from the EEG headset via user input, wherein the computing device comprises hardware implementing a brain-computer interface platform.

* * * * *